US00PP35457P2

(12) United States Plant Patent
Barnes

(10) Patent No.: US PP35,457 P2
(45) Date of Patent: Nov. 7, 2023

(54) CESTRUM PLANT NAMED 'WNCESCORYEL'

(50) Latin Name: *Cestrum corymbosum*
Varietal Denomination: WNCESCORYEL

(71) Applicant: WinGen, LLC, Mustang Ridge, TX (US)

(72) Inventor: Brent D. Barnes, Riverside, CA (US)

(73) Assignee: WinGen llc, Mustang Ridge, TX (US)

( * ) Notice: Subject to any disclaimer, the term of this patent is extended or adjusted under 35 U.S.C. 154(b) by 0 days.

(21) Appl. No.: 18/087,407

(22) Filed: Dec. 22, 2022

(51) Int. Cl.
*A01H 5/02* (2018.01)
*A01H 6/82* (2018.01)

(52) U.S. Cl.
USPC ..... Plt./226

(58) Field of Classification Search
USPC ..... Plt./226, 263.1
CPC ..... A01H 5/02; A01H 5/00; A01H 6/82
See application file for complete search history.

(56) References Cited

U.S. PATENT DOCUMENTS

PP29,607 P2 * 8/2018 Trees ..... Plt./226

* cited by examiner

*Primary Examiner* — June Hwu
(74) *Attorney, Agent, or Firm* — Cassandra Bright

(57) ABSTRACT

A new and distinct cultivar of *Cestrum* plant named 'WNCESCORYEL' is disclosed, characterized by continuous, heavy flowering, and compact plant habit with superior branching and form. The new cultivar is a *Cestrum*, suitable for ornamental garden purposes.

2 Drawing Sheets

Latin name of the genus and species: *Cestrum corymbosum.*

Variety denomination: 'WNCESCORYEL'.

BACKGROUND OF THE INVENTION

The new cultivar is a product of a planned breeding program by the inventor. The self-pollination resulting in the new variety was made during August of 2015, at a nursery in Bonsall, Calif. The parent is the unpatented internal *Cestrum* seedling designated '16BR'. The inventor discovered this new variety at the same nursery in July 2016.

After identifying the new variety as a potentially interesting selection, the inventor first propagated plants of 'WNCESCORYEL' by vegetative tip cuttings during August of 2016 at the same nursery in Bonsall, Calif. Multiple generations have been reproduced and have shown that the unique features of this cultivar are stable and reproduced true to type.

Date of first sale was Jun. 21, 2022, occurring in Grand Haven, Mich. This sale was made directly by the inventor or one who obtained the claimed invention directly or indirectly from the inventor. This sale and all public disclosures made between Jun. 21, 2022 and the filing of this application fall within the exception allowed under 102(b)(1).

SUMMARY OF THE INVENTION

The cultivar 'WNCESCORYEL' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'WNCESCORYEL' These characteristics in combination distinguish 'WNCESCORYEL' as a new and distinct *Cestrum* cultivar:

1. Compact habit with superior branching and form.
2. Heavy flowering.
3. Long bloom period (continuously blooming).

COMPARISON TO PARENT VARIETY

'WNCESCORYEL' is similar in most horticultural characteristics to the parent variety. Plants of the new cultivar 'WNCESCORYEL' however, differ in the following:

1. The new variety has a compact habit with heavy branching, while the parent has a more vigorous habit with less branching.
2. The new variety has greater bloom coverage during flowering period than the parent.
3. The new variety has a longer blooming period than the parent.

BRIEF DESCRIPTION OF THE PHOTOGRAPHS

Figure 1:
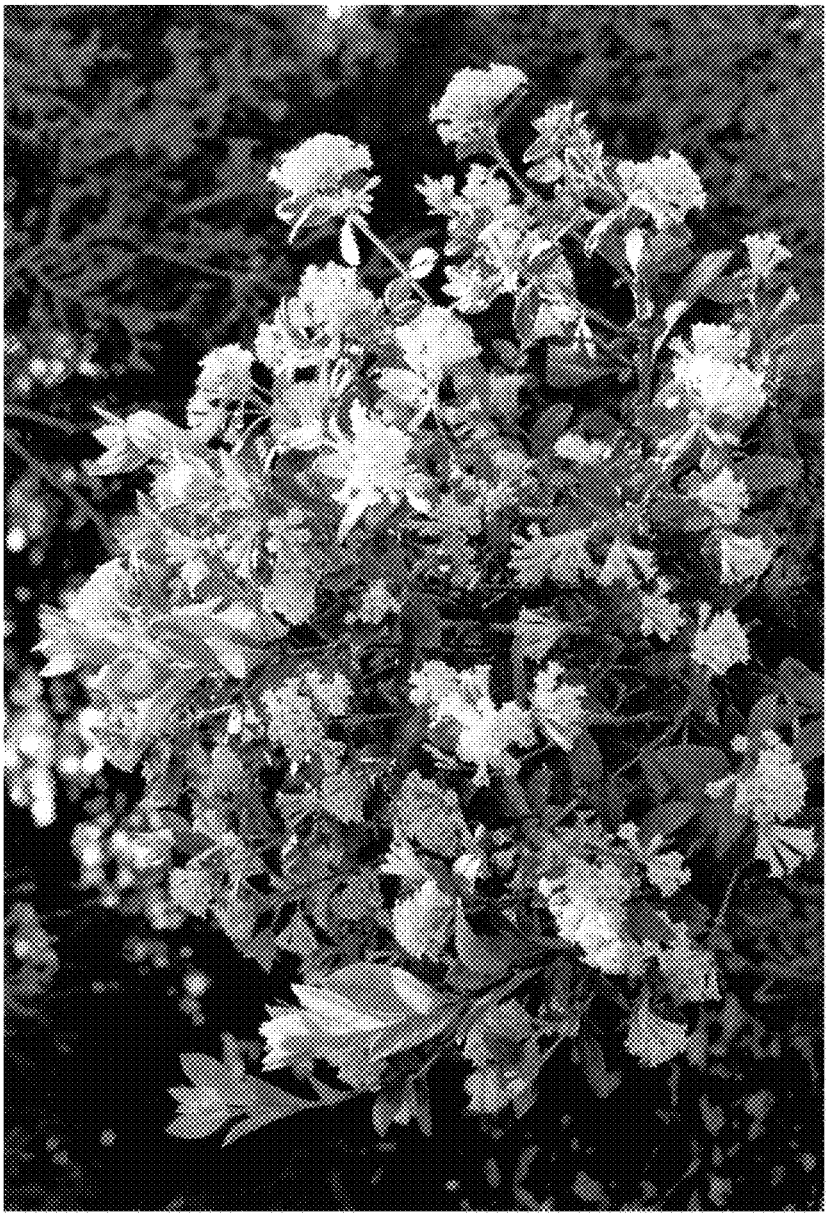

The accompanying photograph in FIG. 1 illustrates in full color a plant of 'WNCESCORYEL' grown outdoors in Grand Haven, Mich.

Figure 2:
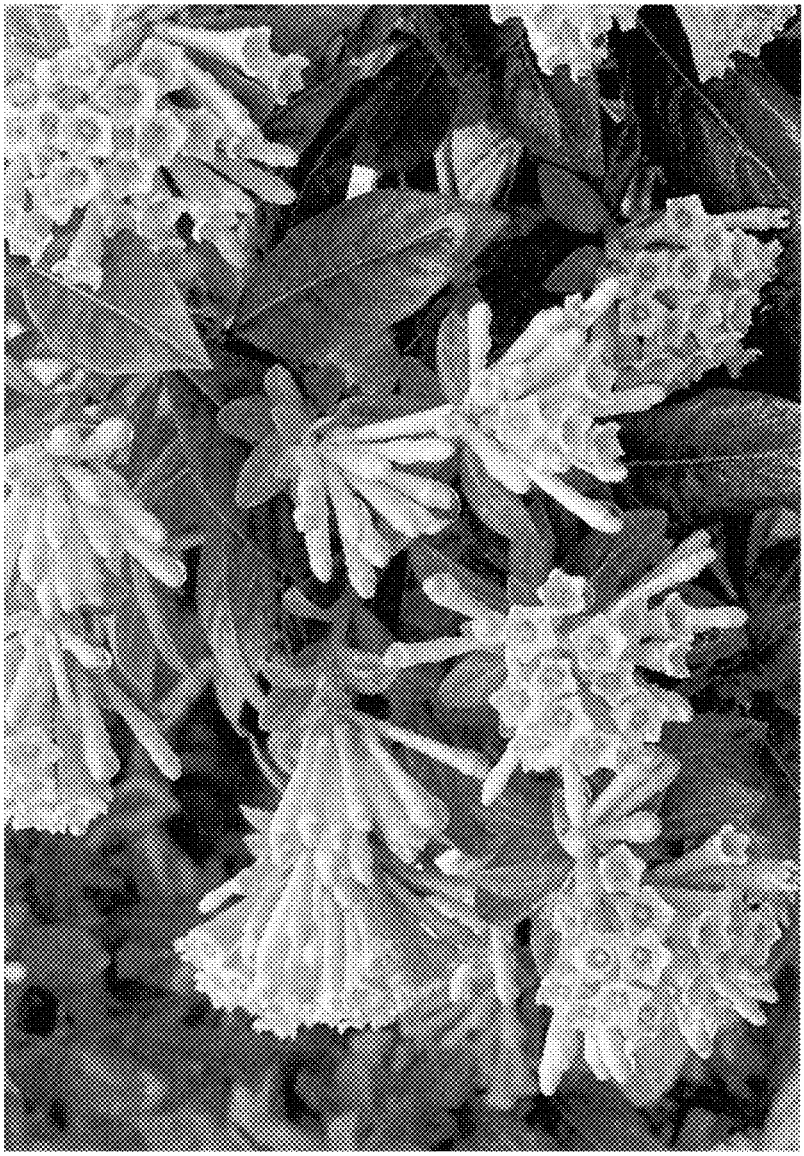

FIG. 2 shows a closer view of flowers on plants of the new variety.

Plants photographed are approximately 2 to 3 years old. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'WNCESCORYEL' plants grown in a poly-greenhouse in Grand Haven, Mich. in November 2021. Plants are approximately 2 to 3 years old, in #3 containers. The average day time temperature is 18-27° C., average night temperature is 5-10° C. Measurements and numerical values represent averages of typical plant types.

Botanical classification: *Cestrum corymbosum* 'WNCESCORYEL'.

PROPAGATION

Method: Vegetative tip cuttings.

Time to rooting: 1 week at 18-27° C. during summer.

Time to produce a rooted plant: 5 to 6 weeks during summer.

Root description: Moderately dense, moderate branching, medium thickness, fibrous. Off-white to tan in color, not accurately measured by the color chart.

PLANT

Plant type: Perennial flowering shrub.

Plant shape: Upright.

Growth habit: Upwards.

Height: 80 cm.

Plant spread: 65 cm.

Growth rate: Good.

Plant vigor: Fairly vigorous.

Branching characteristics:

*Lateral branches*.—Branching Habit: Basal. Quantity: About 20. Length: 60 cm. Diameter. 5 mm.

*Stem*.—Shape: Rounded. Aspect. 70° to 90°. Strength: Strong. Pubescence: Yes, on new growth only. Color: New Growth: RHS Yellow-Green 147B. Old Growth: Near RHS Grey-Brown 199D.

*Internode*.—2 to 1 cm, decreasing from base to tip.

FOLIAGE

Leaf:

*Arrangement*.—Sub-opposite.

*Length*.—7.5 cm.

*Width*.—2.75 cm.

*Shape*.—Oblong.

*Apex*.—Acute.

*Base*.—Cuneate.

*Margin*.—Entire.

*Texture of top surface*.—Lightly pubescent.

*Texture of bottom surface*.—Lightly pubescent with pronounced venation.

*Color*.—Young foliage upper side: RHS Green NN137B. Young foliage under side: RHS Yellow-Green 147B. Mature foliage upper side: RHS Green NN137B. Mature foliage under side: RHS Yellow-Green 147B.

*Venation*.—Type: Pinnate. Venation color upper side: RHS Yellow-Green 147B. Venation color under side: RHS Yellow-Green 147B.

Petiole:

*Length*.—1 cm.

*Diameter*.—2 mm.

*Texture*.—Pubescent.

*Color*.—RHS Yellow-Green 147B with Black 203B.

FLOWER

Bloom period: Summer through fall.

Flowers:

*Arrangement*.—Salverform flowers in terminal corymbs.

*Flowering habit*.—Terminal ends of lateral branches.

*Inflorescence type*.—Corymb.

*Inflorescence height*.—4 cm.

*Inflorescence width*.—6 cm.

*Flower shape*.—Salverform.

*Flower aspect*.—Upright.

*Quantity of flowers per inflorescence*.—About 25 to 50.

*Quantity of flowers per lateral stem*.—100 to 200.

*Quantity of buds per lateral stem*.—About 100.

*Flower diameter*.—7.5 mm.

*Flower depth*.—2 cm.

*Flower throat diameter, top*.—5 mm.

*Flower tube diameter, base*.—2 mm.

*Flower tube length*.—2 cm.

*Flower throat texture*.—Glabrous.

*Flower tube texture*.—Glabrous.

*Flower tube color*.—RHS Yellow-Orange 23B and 23C.

*Flower throat color*.—RHS Yellow-Orange 23B and 23C.

*Persistent or self-cleaning*.—Self-cleaning.

*Fragrance*.—Light and sweet.

Petals:

*Length*.—2 mm from throat.

*Width*.—2 mm.

*Apex*.—Acute.

*Shape*.—Triangular.

*Margin*.—Entire.

*Arrangement*.—Whorl of 5, stellate.

*Number*.—5.

*Appearance*.—Glabrous.

*Texture*.—Glabrous.

*Color*.—Upper surface at first opening: RHS Yellow-Orange 23B. Under surface at first opening RHS Yellow-Orange 23C. Upper surface at maturity: RHS Yellow-Orange 23B. Under surface at maturity: RHS Yellow-Orange 23C.

Petaloids: Absent.

Bud:

*Shape*.—Linear, flared tip.

*Length*.—1.75 cm.

*Diameter*.—3 mm.

*Aspect*.—Upright.

*Color*.—RHS Yellow 13B and 13C.

Sepals:

*Length*.—Less than 1 mm.

*Width*.—Less than 1 mm.

*Apex*.—Acute.

*Base*.—Fused.

*Shape*.—Triangular.

*Margin*.—Entire.

*Arrangement*.—Whorl of 5, stellate.

*Number*.—5.

*Appearance*.—Diminutive (less than 1 mm), triangular.
*Texture*.—Lightly pubescent.
*Color*.—Upper surface: RHS Green-Yellow 1C. Under surface: RHS Green-Yellow 1C.
*Calyx shape*.—Collar-like.

Peduncle:
*Length*.—2 cm.
*Diameter*.—2 mm.
*Color*.—RHS Yellow-Green 144B.
*Texture*.—Pubescent.
*Angle*.—90°.
*Strength*.—Good.

Pedicel:
*Length*.—1.5 mm.
*Diameter*.—1 mm.
*Color*.—RHS Yellow-Green 144B.
*Texture*.—Pubescent.
*Angle*.—45°.
*Strength*.—Good, somewhat flexible.

REPRODUCTIVE ORGANS

Stamens:
*Number*.—5.
*Filament length*.—5 mm.
*Filament color*.—RHS Yellow-Orange 19C.
*Anthers*.—Length: 1 mm. Color: RHS Greyed-Orange 174A. Pollen: Quantity: Sparse. Color: RHS White 155A. Shape: Round.

Pistil:
*Number*.—1.
*Length*.—1.5 cm.
*Style*.—Length: less than 1 mm. Color: RHS White 155A.
*Stigma*.—Shape: Rounded. Color: RHS Yellow-Green 144B.

OTHER CHARACTERISTICS

Disease and pest resistance: Neither resistance nor susceptibility to normal diseases and pests of *Cestrum* observed.
Temperature tolerance: Cold tolerance to −31° C. Heat tolerance to 38° C.
Fruit/seed: Not observed.

What is claimed is:

1. A new and distinct cultivar of *Cestrum* plant named 'WNCESCORYEL' as herein illustrated and described.

* * * * *